United States Patent
Huang et al.

(10) Patent No.: US 10,051,163 B2
(45) Date of Patent: Aug. 14, 2018

(54) 180 DEGREE BENDABLE ARTICULATING BORESCOPE ENDOSCOPE

(71) Applicant: Oasis Scientific, Taylors, SC (US)

(72) Inventors: Changzheng Huang, Shenzhen Guangdong (CN); Liang Zhao, Tianjin (CN); Haibin Deng, Shenzhen Guangdong (CN)

( * ) Notice: Subject to any disclaimer, the term of this patent is extended or adjusted under 35 U.S.C. 154(b) by 335 days.

(21) Appl. No.: 14/974,022

(22) Filed: Dec. 18, 2015

(65) Prior Publication Data

US 2016/0182776 A1    Jun. 23, 2016

(30) Foreign Application Priority Data

Dec. 19, 2014    (CN) .......................... 2014 1 0796062

(51) Int. Cl.
*G02B 23/24* (2006.01)
*H04N 5/225* (2006.01)
*A61B 1/005* (2006.01)

(52) U.S. Cl.
CPC ......... *H04N 5/2252* (2013.01); *A61B 1/0055* (2013.01); *G02B 23/2476* (2013.01); *H04N 5/2253* (2013.01); *H04N 2005/2255* (2013.01)

(58) Field of Classification Search
None
See application file for complete search history.

(56) References Cited

U.S. PATENT DOCUMENTS

| | | | | |
|---|---|---|---|---|
| 2007/0232858 A1* | 10/2007 | Macnamara | ......... | A61B 1/0052 600/149 |
| 2008/0249364 A1* | 10/2008 | Korner | ............... | A61B 1/00071 600/141 |
| 2009/0171159 A1* | 7/2009 | Jorgensen | ............ | A61B 1/0055 600/139 |
| 2010/0262075 A1* | 10/2010 | Danitz | ................. | A61B 1/0053 604/95.04 |
| 2014/0364024 A1* | 12/2014 | Hartelius | ................ | B63B 35/73 441/129 |
| 2016/0135982 A1* | 5/2016 | Garcia | .................. | A61F 5/4404 600/581 |
| 2017/0049298 A1* | 2/2017 | Hunter | .................... | A61B 1/005 |
| 2017/0197060 A1* | 7/2017 | Houck | .............. | A61M 25/0147 |

* cited by examiner

*Primary Examiner* — Jay Patel
*Assistant Examiner* — Shadan E Haghani
(74) *Attorney, Agent, or Firm* — Southeast IP Group, LLC; Thomas L. Moses

(57) ABSTRACT

An articulating digital endoscope or borescope which can be bent up to 180 degrees and has a small bending radius, simple structure, and can be operated with one hand. The front end of the bending part is connected to a digital camera, the rear end of the bending part is connected to the main body and the handle of the endoscope. The bending part comprises the upper and lower connecting segments, a number of joint plates and in-between discs connected in sequence. There are concave and convex structures on both sides of the joint plates so that the joint plates can fit to each other and be rotated. A mechanical shutter release cable is used to connect the bending part, the endoscope main body and the handle. When the shutter button is pressed, the inner spring of the shutter pushes forward to bend the bending part.

7 Claims, 4 Drawing Sheets

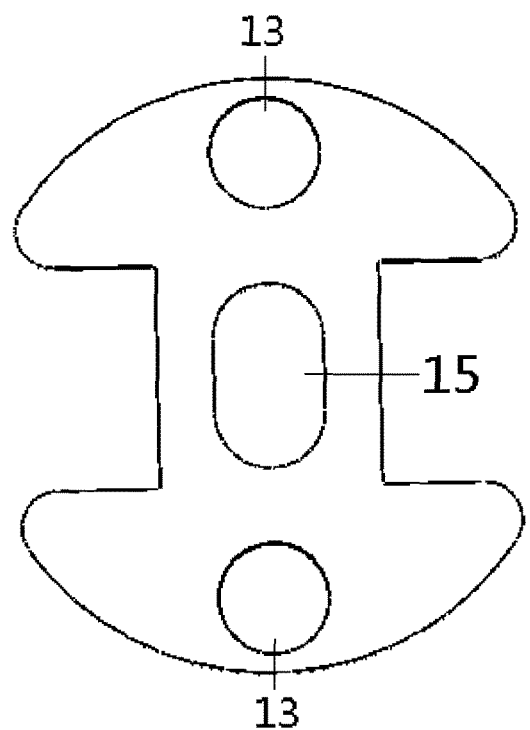
Figure 5.
Figure 6.
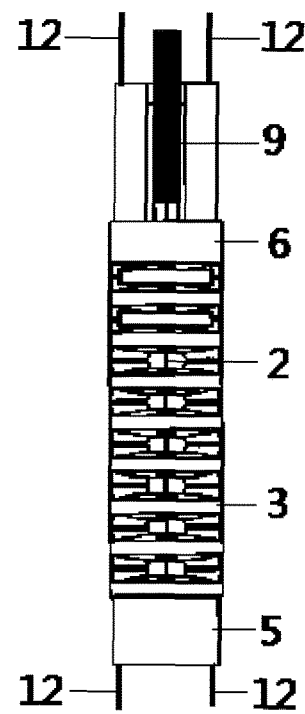

180 DEGREE BENDABLE ARTICULATING BORESCOPE ENDOSCOPE

TECHNICAL FIELD

The present invention relates to an endoscope, specifically relates to an articulating digital endoscope.

BACKGROUND

The endoscope is a well-known testing equipment used to explore places which are difficult to be seen directly by the human eye. The endoscopes with articulation on the front end are especially useful in practice. However, the articulation endoscopes are not widely due to their complex design structures, difficulty to assemble and produce, complicated processes, and high market prices.

The current flexible bendable digital endoscope products on the market are typically made of deformable metal tubes. The metal tube bendable endoscopes are bended by hand, like bending a lamp holder. Once it is inserted into a cylinder, one can no longer change the bending angles. The disadvantages of these metal tube endoscopes are that the bending radius is too large, it is difficult to observe the inside of small areas, difficult to achieve 180-degree bending, and both hands are needed to operate which is very inconvenient.

BRIEF DESCRIPTION OF THE FIGURES

These and other features, aspects, and advantages of the present invention will become better understood with regard to the following description, appended claims, and accompanying drawings where:

FIG. 5 is a top view of a preferred embodiment of the in-between discs of the bending part shown in FIG. 1; and FIG. 6 is a schematic view of a preferred embodiment of the pulling cable of the bending part shown in FIG. 1.

BRIEF SUMMARY OF THE INVENTION

Figure 1:
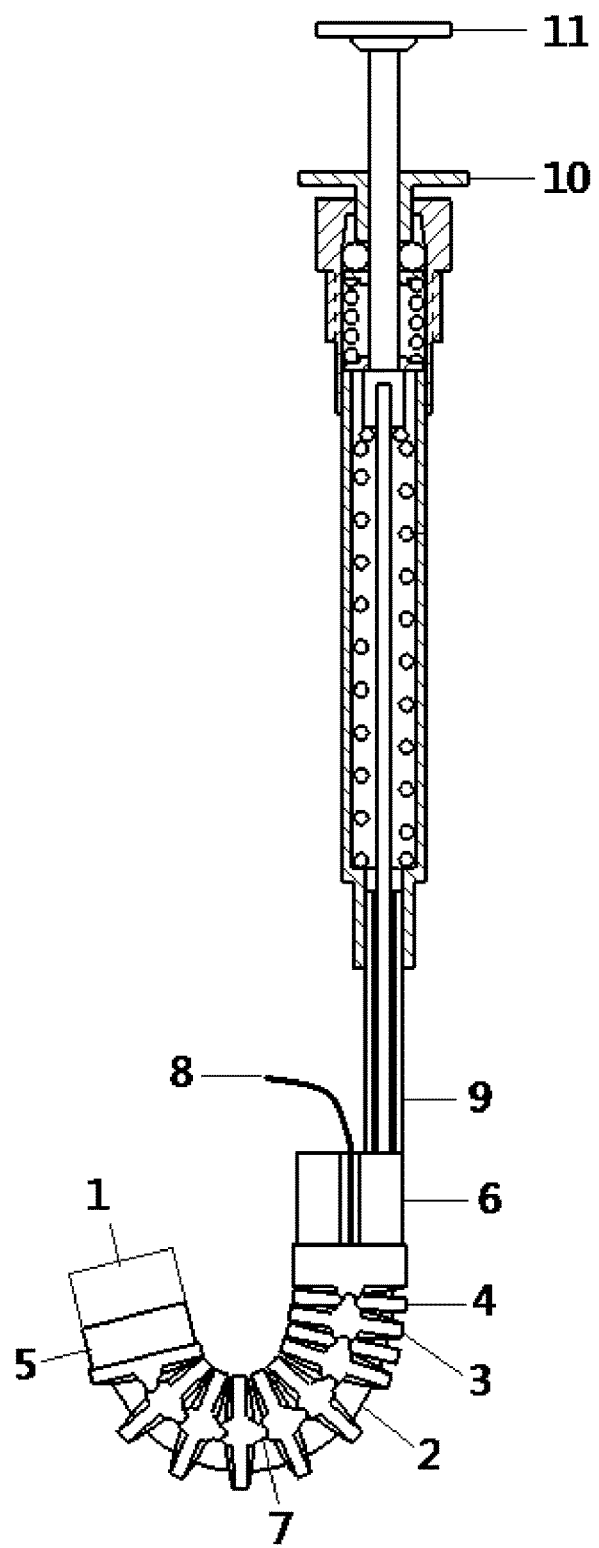
FIG. 1 is a schematic side view of a preferred embodiment of the overall assembly structure of this invention.

To overcome the deficiencies of the prior art as described above, the present invention provides an articulating digital endoscope which is structurally simple, easy to manufacture, has a smaller bending radius, has a larger bending angle, and can be operated with one hand.

The objectives of the present invention are achieved by the following technical designs: The articulating digital endoscope from bottom to top comprises a digital camera, a bending part, an endoscope main body and a handle. An endoscope main body refers to the endoscope part which can go through a small opening into the area which is to be examined. The front end of the bending part is connected to a digital camera, and the rear end of the bending part is connected to the endoscope main body. In a preferred embodiment, the bending part consists of the following components connected in series sequence: the upper connecting segment, a number of joint plates, in-between discs and a lower connecting segment. On the both sides of each bending part component there are pulling holes; two flexible lines are pulled through each hole of each bending part component and assemble these bending part components together. There are in-between discs between the first and the second joint plates near the upper connecting segment, whose function is to prevent excessive rotation of the first and second joint plates. The function of the in-between discs can also be achieved by changing the shapes of the first and second joint plates. There are convex and concave structures on the contacting surfaces of both the upper and lower connecting segments, and on the both sides of the joint plates. These convex and concave structures can be fitted tightly on the upper and lower connecting segments, the double-sided surfaces of the joint components. Pulling the flexible pulling lines causes the convex and concave of the joint components to engage each other, to fit closely and to rotate easily. A hole is made in the center of each bending part component to be used to pass through the cables used to connect the digital camera and endoscope man body. There are two pushing holes on the two sides of each bending part component, which are at right direction of the pulling holes. A mechanical shutter cable is used to connect the bending part, endoscope body and handle in sequence. A shutter release button is provided at the rear end of the handle for easy thumb operation; the shutter cable sequentially passes through the handle, the endoscope main body, and the outer spring cable is fixed on the pushing hole of the upper connecting segment, the inner spring cable continues to pass through the in-between disc, the pushing holes on the joint plates, and is fixed on the lower connecting segment. When the shutter button is pressed, the shutter cable inner spring pushes the lower connecting segment down at one side of the bending part to cause the rotation of concave convex structures of the joint plates and the bending part is bent. The shutter locking mechanism can lock the bending part at any bending angle.

Compared with the prior art the present invention has the following advantageous functions and features:

1. The outstanding feature of this invention is the design of a novel bending part. The bending part uses pulling cable assembled joint plates, the concave-convex structures on the surfaces of joint plates which can be rotated freely, and the pushing and pulling holes to achieve 180 degree bending of the endoscope distal end. The bending radius is controlled within a small range. The structure is compact and small, and easy to be constructed at low cost. The endoscope is suitable for many applications.

2. Another unique feature of this invention is to skillfully use the camera's mechanical shutter cable to control the bending of the distal end. The shutter cable is lightweight and easy to operate, which makes the inventive articulating endoscope bend freely and easily. The shutter cable locking mechanism is used to lock the bending angles, which is simple, reliable, low cost, easily portable and very effective. The shutter cable design makes bending, straightening, locking/unlocking and other functions capable of being operated with one hand.

DETAILED DESCRIPTION OF THE INVENTION

Figure 2:
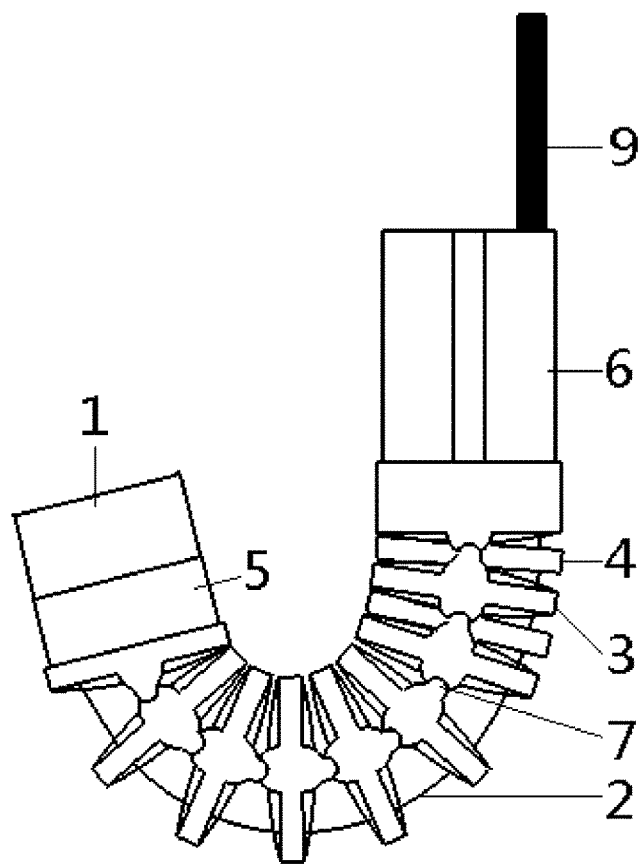
FIG. 2 is a schematic side view of a preferred embodiment of the bending part shown in FIG. 1.
Figure 3:
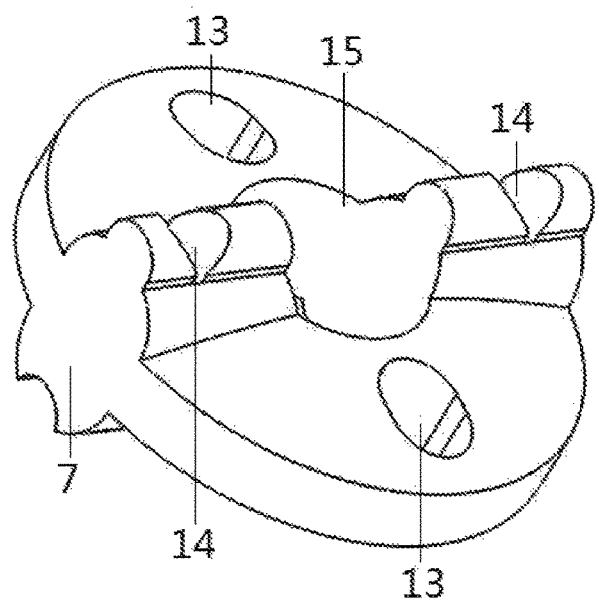
FIG. 3 is a schematic perspective view of a preferred embodiment of the circular joint plates of the bending part shown in FIG. 1.
Figure 4:
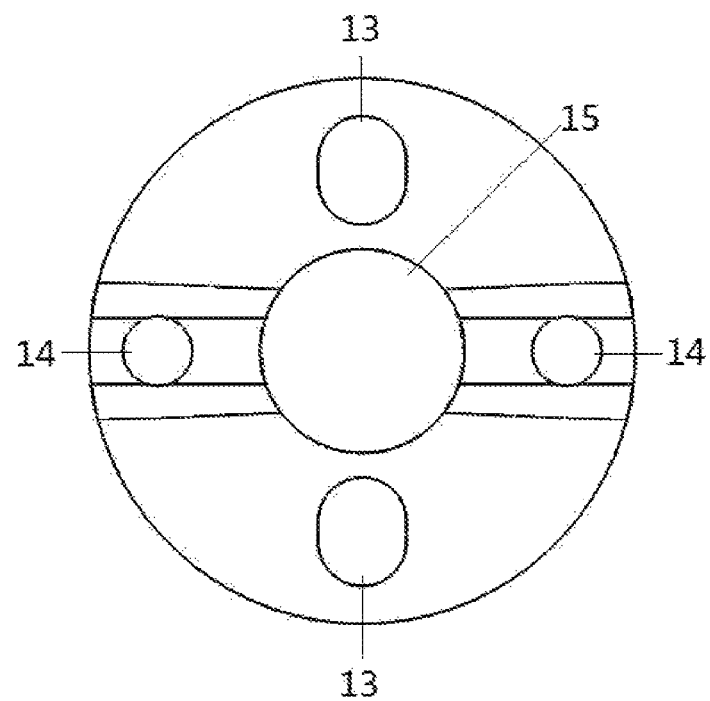
FIG. 4 is a top view of a preferred embodiment of the circular joint plates of the bending part shown in FIG. 3.

A preferred embodiment of the present invention is further described with the following operational example and drawings:

As shown in FIG. 1, FIG. 2, FIG. 3, FIG. 4, FIG. 5, and FIG. 6: The present inventive articulating digital endoscope can bend up to 180 degrees, and there is a novel and unique bending part at the distal end of the endoscope. In a preferred embodiment, the front end of the bending part is connected to a digital camera (1), and the rear end of the bending part is connected to the main body of the endoscope. The digital camera moves with the bending part when the bending part is bent. The bending part preferably comprises following components operably connected together: an upper connecting segment (6), a number of joint plates (3), in-between discs (4) and a lower connecting segment (5). The upper connecting segment (6) is connected to the endoscope main body, and the lower connecting segment (5) is connected to a digital camera (1). There is a pulling hole (14) on each side of two sides of each bending part component. The pulling cable line (12) sequentially passes through the pulling holes (14) of each bending component to pull and assemble the bending part components together. There is an in-between disc (4) between the first and second circular joint plates, and the role of the in-between disc is to prevent the first and second circular joint plates from over rotating to side directions. On both end surfaces of the upper and lower connecting segments connecting to the joint plates, and on the two are surfaces of each joint plate, a linear convex and concave structure (7) is constructed, positioning the line connecting the two pulling holes (14) on an axis. Pulling the pulling cable line (12) will make the corresponding concave and convex structures (7) engage each other to fit tightly and rotate freely. Each individual bending part component has a central hole (15) for the digital camera cable (8) to connect the digital camera and for the endoscope main body to go through. On both sides of each bending part component in the cross right direction of the pulling holes are two pushing holes (13). The present invention uses a mechanical shutter assembly cable to connect the bending part components, the endoscope main body and handle. The shutter button (11) is at the rear end of the handle for easy thumb operation. The shutter cable sequentially passes through the handle and the endoscope main body. The outer spring cable (9) is secured with the upper connecting segment on the pushing hole (13), the inner spring cable continues to pass through the pushing holes (13) of the in-between disc (4) and the joint plates (3), and is secured with the lower connection segment (5). Pressing the shutter button (11) will push the inner spring (2) down on each bending part component at one side of the bending part through the pushing holes (13), which causes the concave-convex structure (7) to rotate and the whole bending part to bend. When the locking device (10) of the shutter cable is on, pressing the shutter button (11) will lock the bending part at any bending angle.

Although the articulating endoscope of the present invention has been described in detail with reference to particular embodiments and dimensions, the embodiments are for illustrative purposes only and do not limit the invention. It is to be appreciated that those skilled in the art can change or modify the embodiments without departing from the scope and spirit of the invention. It is to be understood that the inventive concept is not to be considered limited to the constructions and dimensions disclosed herein.

The terms used in the present application are merely used to describe particular embodiments, and are not intended to limit the present invention. An expression used in the singular encompasses the expression of the plural, unless it has a clearly different meaning in the context. In the present application, it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

What is claimed is:

1. An articulating digital borescope endoscope comprising:
    an endoscope main body
    a bending part operably connected at a proximal end to a distal end of said endoscope main body;
    a digital camera operably connected to a distal end of said bending part;
    wherein said bending part comprises:
    an upper connecting segment operably connected at a first end to said distal end of said endoscope main body, and operably connected at a second end to a first joint plate;
    at least one in-between disc operably connected between said first joint plate and a second joint plate, said second joint plate being operably connected to a plurality of joint plates operably connected to one another; and
    a last joint plate operably connected at a first end to said plurality of joint plates and operably connected at a second end to a first end of a lower connecting segment;
    wherein said digital camera is fixed to a second end of said lower connecting segment;
    a mechanical shutter release cable comprising an outer spring fixed to said upper connecting segment and an inner spring, wherein said inner spring successively passes through said outer spring and a pushing hole in said upper connecting segment, in-between disc, and joint plates, and affixes to said lower connecting segment;
    a shutter button having an engaged position and a released position, said shutter button operably connected to said shutter release cable such that when said shutter button is pressed into said engaged position, said outer spring provides resistance to said shutter button and said inner spring pushes down one side of said lower connecting segment, prompting said joint plates to rotate and said bending part to bend and such that releasing said shutter button causes said outer spring to push said shutter button back to said released position and said bending part to return to a generally straight position, steering said digital camera without tension cables.

2. The apparatus of claim 1, wherein said upper connecting segment, said lower connecting segment, and said joint plates are rotatably connected by concave and convex joining structures.

3. The apparatus of claim 2, wherein opposing sides of each of said upper connecting segment, joint plates, in-between disc, and lower connecting segment include one of said pushing holes at a 90 degree angle to said joining structures.

4. The apparatus of claim 1, wherein said bending part includes a central hole for passing a cable to connect to and operate said digital camera.

5. The apparatus of claim 1, further including a shutter locking device operably connected to said bending part for locking said bending part at a bending angle.

6. The apparatus of claim 1, further including a means for locking said bending part at a bending angle.

7. An articulating digital borescope endoscope comprising:
    an endoscope main body
    a bending part operably connected at a proximal end to a distal end of said endoscope main body;

a digital camera operably connected to a distal end of said bending part;

wherein said bending part comprises:

an upper connecting segment operably connected at a first end to said distal end of said endoscope main body, and operably connected at a second end to a first joint plate;

at least one in-between disc operably connected between said first joint plate and a second joint plate, said second joint plate being operably connected to a plurality of joint plates operably connected to one another; and a last joint plate operably connected at a first end to said plurality of joint plates and operably connected at a second end to a first end of a lower connecting segment;

wherein said digital camera is fixed to a second end of said lower connecting segment;

wherein said upper connecting segment, said lower connecting segment, and said joint plates are rotatably connected by convex and concave joining structures;

wherein each of said upper connecting segment, joint plates, in-between disc, and lower connecting segment further include a central hole for passing a cable to connect to and operate said digital camera;

wherein each of said upper connecting segment, joint plates, in-between disc, and lower connecting segment further include pushing holes disposed on opposing sides of said central hole and at 90 degree angles to said joining structures;

a mechanical shutter release cable comprising an outer spring fixed to said upper connecting segment and an inner spring, wherein said inner spring successively passes through said outer spring and one of said pushing holes in each of said upper connecting segment, in-between disc, and joint plates, and affixes to said lower connecting segment;

a shutter button having an engaged position and a released position, said shutter button operably connected to said shutter release cable such that when said shutter button is pressed into said engaged position, said outer spring provides resistance to said shutter button and said inner spring pushes down one side of said lower connecting segment, prompting said joint plates to rotate, and said bending part to bend and such that releasing said shutter button causes said outer spring to push said shutter button back to said released position and said bending part to return to a generally straight position; and a shutter locking device operably connected to said bending part for locking said bending part at a bending angle.

* * * * *